(12) United States Patent
Hardy (10) Patent No.: US 11,451,948 B2
(45) Date of Patent: Sep. 20, 2022

(54) MEDICAL ALERT APPLICATION

(71) Applicant: Jeffery Les Hardy, Surrey (CA)

(72) Inventor: Jeffery Les Hardy, Surrey (CA)

(73) Assignee: Jeffery Les Hardy, Surrey (CA)

( * ) Notice: Subject to any disclaimer, the term of this patent is extended or adjusted under 35 U.S.C. 154(b) by 0 days.

(21) Appl. No.: 16/960,065

(22) PCT Filed: Jan. 4, 2019

(86) PCT No.: PCT/CA2019/050011
§ 371 (c)(1),
(2) Date: Jul. 3, 2020

(87) PCT Pub. No.: WO2019/134045
PCT Pub. Date: Jul. 11, 2019

(65) Prior Publication Data
US 2021/0058760 A1  Feb. 25, 2021

Related U.S. Application Data

(60) Provisional application No. 62/613,718, filed on Jan. 4, 2018.

(51) Int. Cl.
*H04W 4/90* (2018.01)
*G16H 10/60* (2018.01)
*H04W 4/029* (2018.01)
*G10L 13/00* (2006.01)

(52) U.S. Cl.
CPC .............. *H04W 4/90* (2018.02); *G10L 13/00* (2013.01); *G16H 10/60* (2018.01); *H04W 4/029* (2018.02)

(58) Field of Classification Search
CPC ........ H04W 4/90; H04W 4/029; G16H 10/60; G16H 13/00; G10L 13/00
USPC ....................................................... 455/404
See application file for complete search history.

(56) References Cited

U.S. PATENT DOCUMENTS

| 8,345,665 B2 | 1/2013 | Vierir et al. | |
| 2005/0070315 A1* | 3/2005 | Rai ......................... | H04W 4/90 455/404.1 |
| 2012/0101847 A1* | 4/2012 | Johnson ................. | G06Q 30/00 705/3 |

(Continued)

OTHER PUBLICATIONS

"NOverdose—Someone's life depends on you!" Internet Archive; Wayback Machine, Oct. 14, 2017 (Oct. 14, 2017), pp. 1-7, [online] [retrieved on Apr. 8, 2019 Apr. 8, 2019)]. Retrieved from the Internet: https://web.archive.org/web/20171014142821/http://noverdoseapp.com/ pp. 1, 2, 4, 6.

*Primary Examiner* — Ted M Wang
(74) *Attorney, Agent, or Firm* — Lawrence Chan; Oyen Wiggs Green & Mutala LLP (57) ABSTRACT

A mobile application designed to operate on a mobile device. The user, through a user interface, inputs the drug being taken, and activates a start input. This begins a timer that runs down from a predetermined amount of time. If the user does not activate a stop input before the timer runs out of time, an alert is generated. This alert may be displayed on the user interface. In addition, emergency personnel are contacted. Information regarding the user, the drug taken, and the location of the mobile device may be transmitted to the emergency personnel so that medical assistance may be provided.

5 Claims, 10 Drawing Sheets

(56) References Cited

U.S. PATENT DOCUMENTS

2015/0137972 A1\* 5/2015 Nepo ................ G08B 25/10
340/539.13

\* cited by examiner

MEDICAL ALERT APPLICATION

FIELD OF THE INVENTION

The present invention relates to a system for communicating medical alerts, and in particular, a system for communicating medical alerts for people who may be unable to do so themselves.

BACKGROUND OF THE INVENTION

When a person is in medical distress, such as a result of a drug overdose, it is imperative that medical assistance be provided as soon as possible. However, in many instances, that person may be physically incapable of requesting medical assistance, and if that person is alone, there may not be anyone around to request medical assistance on behalf of that person.

There is therefore a desire for a system that is able to alert relevant authorities even in the event that a person is physically incapable of doing so himself or herself.

SUMMARY OF THE INVENTION

In one embodiment, the invention comprises a mobile application designed to operate on a mobile device. The user, through a user interface, inputs the drug being taken, and activates a start input. This begins a timer that runs down from a predetermined amount of time. If the user does not activate a stop input before the timer runs out of time, an alert is generated. This alert may be displayed on the user interface. In addition, emergency personnel are contacted. Information regarding the user, the drug taken, and the location of the mobile device may be transmitted to the emergency personnel so that medical assistance may be provided.

In another embodiment, a method for alerting emergency personnel in the event of medical distress by a user comprises the steps of providing a mobile application for use on a mobile device; recording, by the mobile application, of a location of the user and a drug taken by the user; initiating, by the user, a timer with a predetermined amount of time; upon the timer expiring without any further input by the user, transmitting, by the mobile application, a message to a remote server, the location of the user and the drug taken; converting, by the remote server, the message into an audio message; determining, by the remote server, an appropriate one of emergency personnel to contact, based, at least in part, on the location of the user; contacting, by the remote server, the appropriate emergency personnel; and transmitting the audio message to the appropriate emergency personnel.

In yet another embodiment, the step of recording, by the mobile application, of the location of the user and the drug taken by the user further comprises recording of a name of the user and a current time.

In a further embodiment, the location of the user may be determined by a location detection sensor located on the mobile device.

In yet a further embodiment, the location detection sensor is a Global Positioning System sensor.

In another embodiment, the step of converting, by the remote server, the message into the audio message is done using a text-to-voice converter.

The foregoing was intended as a summary only and of only some of the aspects of the invention. It was not intended to define the limits or requirements of the invention. Other aspects of the invention will be appreciated by reference to the detailed description of the preferred embodiments.

BRIEF DESCRIPTION OF THE DRAWINGS

The invention will be described by reference to the detailed description of the embodiments and to the drawings thereof in which.

DETAILED DESCRIPTION OF THE INVENTION

The present invention may be implemented in numerous ways, including as a process, an apparatus, a system, or as a computer program embodied on a computer-readable storage medium. Furthermore, the present invention may also be implemented using a processor, such as through a process configured to execute instructions stored on and/or provided by a memory coupled to the processor.

Figure 1:
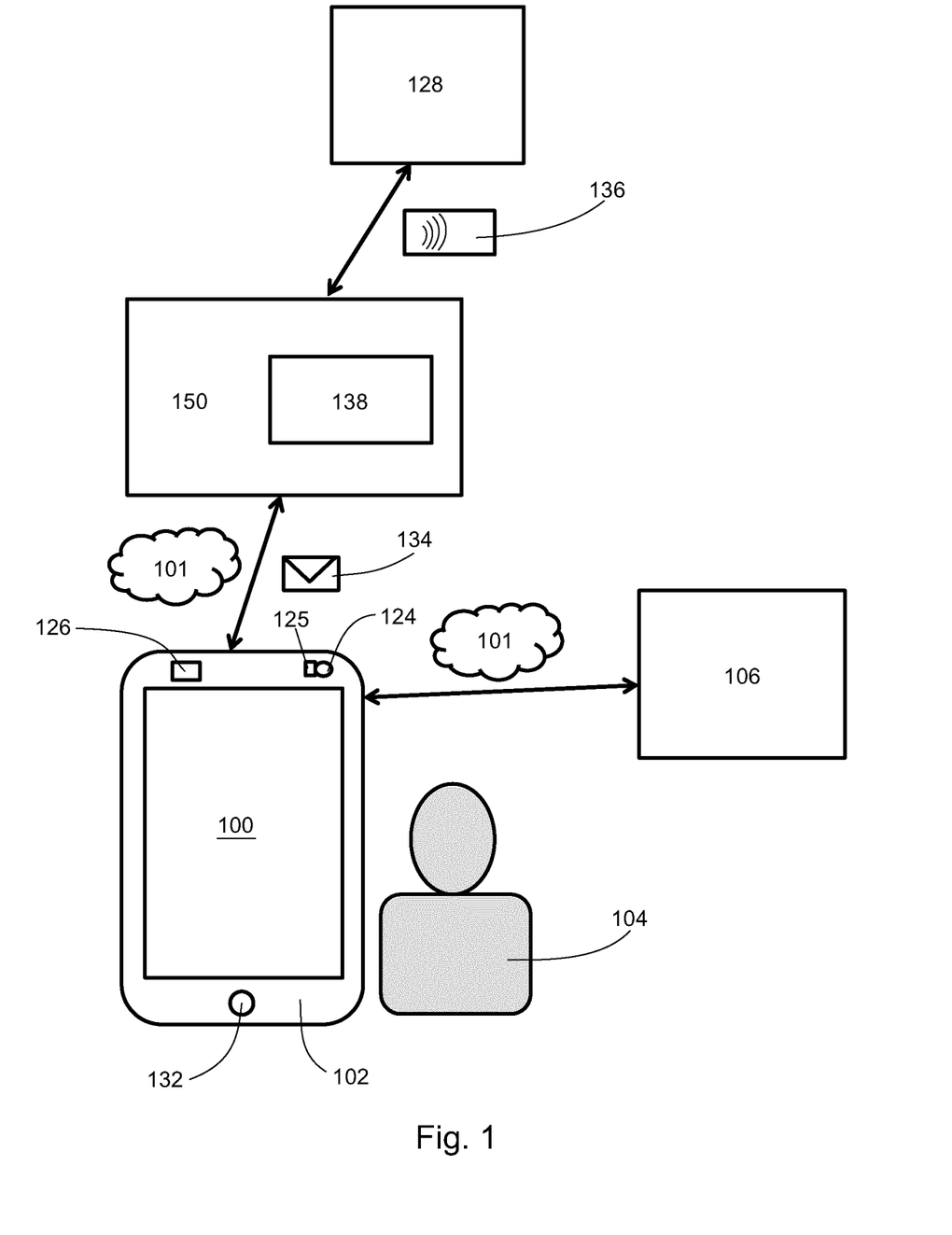
FIG. 1 is a block diagram showing the invention.

Referring to FIG. 1, according to one embodiment, the invention comprises a mobile application 100 that operates on a mobile device 102. The mobile device 102 may include smartphones, tablets, or the like. One or more users 104 of the mobile device 102 may obtain, through network 101, a copy of the mobile application 100 suitable for their mobile device 102 by accessing an appropriate software distribution service 106. For example, if the mobile device 102 operates on the iOS operating system, then the appropriate software distribution service 106 may be the Apple App Store. Similarly, if the mobile device 102 operates on the Android operating system, then the appropriate software distribution service 106 may be the Google Play Store. The network 101 may be the Internet or some other appropriate communications network.

Once the mobile application 100 has been installed on the mobile device 102, the mobile application 100 is ready to be executed.

When the mobile application 100 is executed, the mobile application 100 preferably generates a user interface 108 that allows the user 104 to interact with the mobile application 100. The user interface 108 may initially display an initialization image to greet the user 104. The initialization image may be customized by the user 104 if desired.

Figure 2:
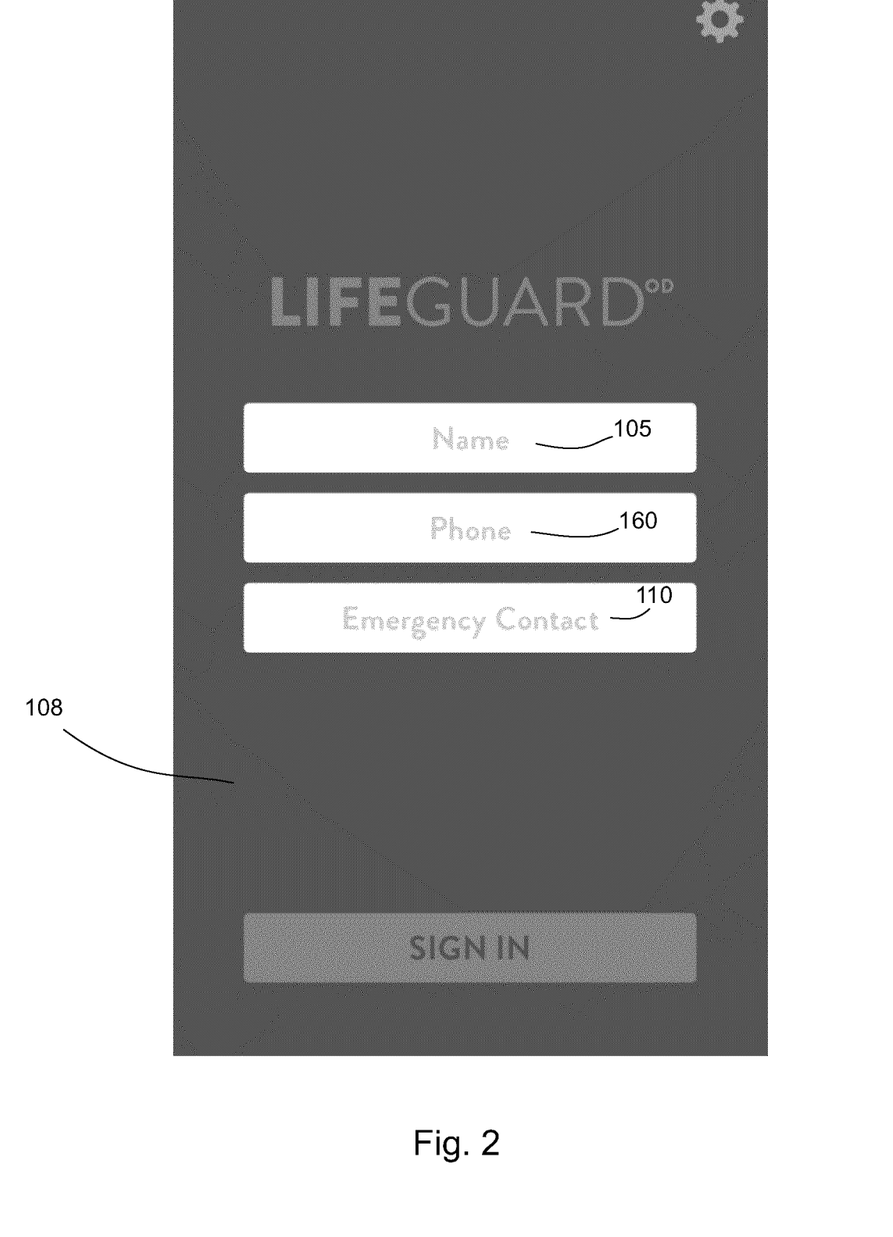
FIG. 2 is a screenshot depicting the user interface of the mobile application prompting the user to input identifying information in accordance with the invention.

Referring to FIG. 2, the user interface 108 preferably prompts the user 104 to input identifying information 105 (e.g. the name of the user 104). The user interface 108 may also prompt the user 104 to input user contact information 160 (e.g. the phone number of the mobile device 102) and also preferably prompts the user 104 to input emergency contact information 110. The emergency contact information 110 may comprise a phone number, an email address, or some other contact information for an emergency contact. The identifying information 105 and/or the emergency contact information 110 may be stored on the mobile device 102 or they may be communicated to a remote server 150 over network 101. The identifying information 105 may also be used to register the user 104 with the mobile application 100 to allow the user 104 to more easily log onto the mobile application 100 in the future.

The user interface 108 may also prompt the user 104 to enter a location of the user 104 (e.g. street address and suite number, if applicable). In the event that the mobile device 102 is equipped with location detection sensors 126 (e.g. Global Positioning System, or GPS, devices, etc.), the mobile application 100 may use the location detection sensors 126 to determine the coordinates of the mobile device 102 and use such coordinates to determine a street address.

The mobile application 100 may then display, through the user interface 108, legal information, for the user 104 to read.

Figure 3:
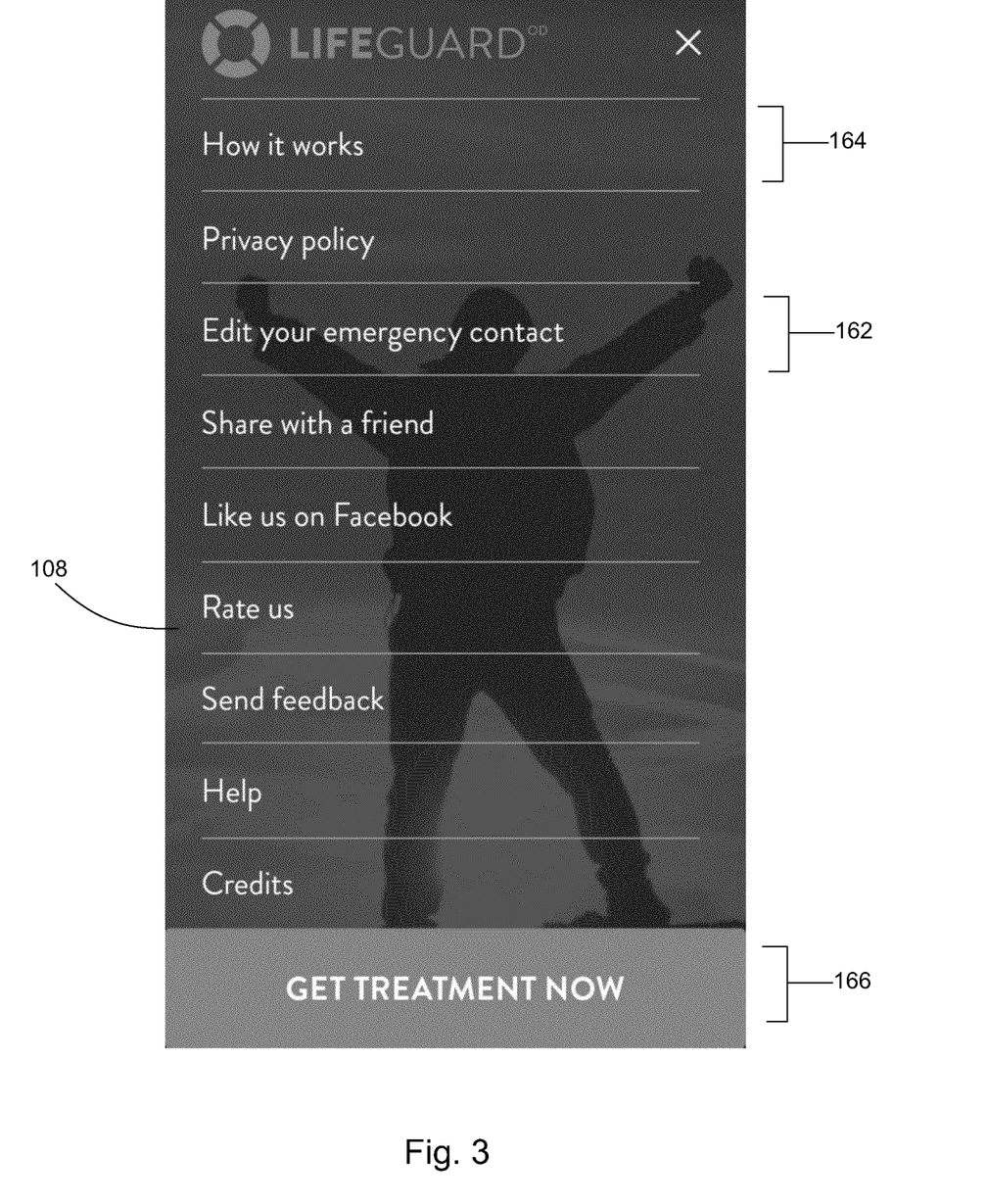
FIG. 3 is a screenshot depicting the user interface showing the preferences for the mobile application.

Referring to FIG. 3, the user interface 108 may also provide the user 104 with the option to view and edit preferences for the mobile application 100. These preferences may allow the user 104 to edit various fields, such as emergency contact information 110 (which may be done through an edit contact information link 162. The preferences may also include information for the user 104, such as instructions on using the mobile application 100 (accessible via an instructions link 164) and instructions on seeking medical treatment information (accessible via a medical treatment link 166).

Figure 4:
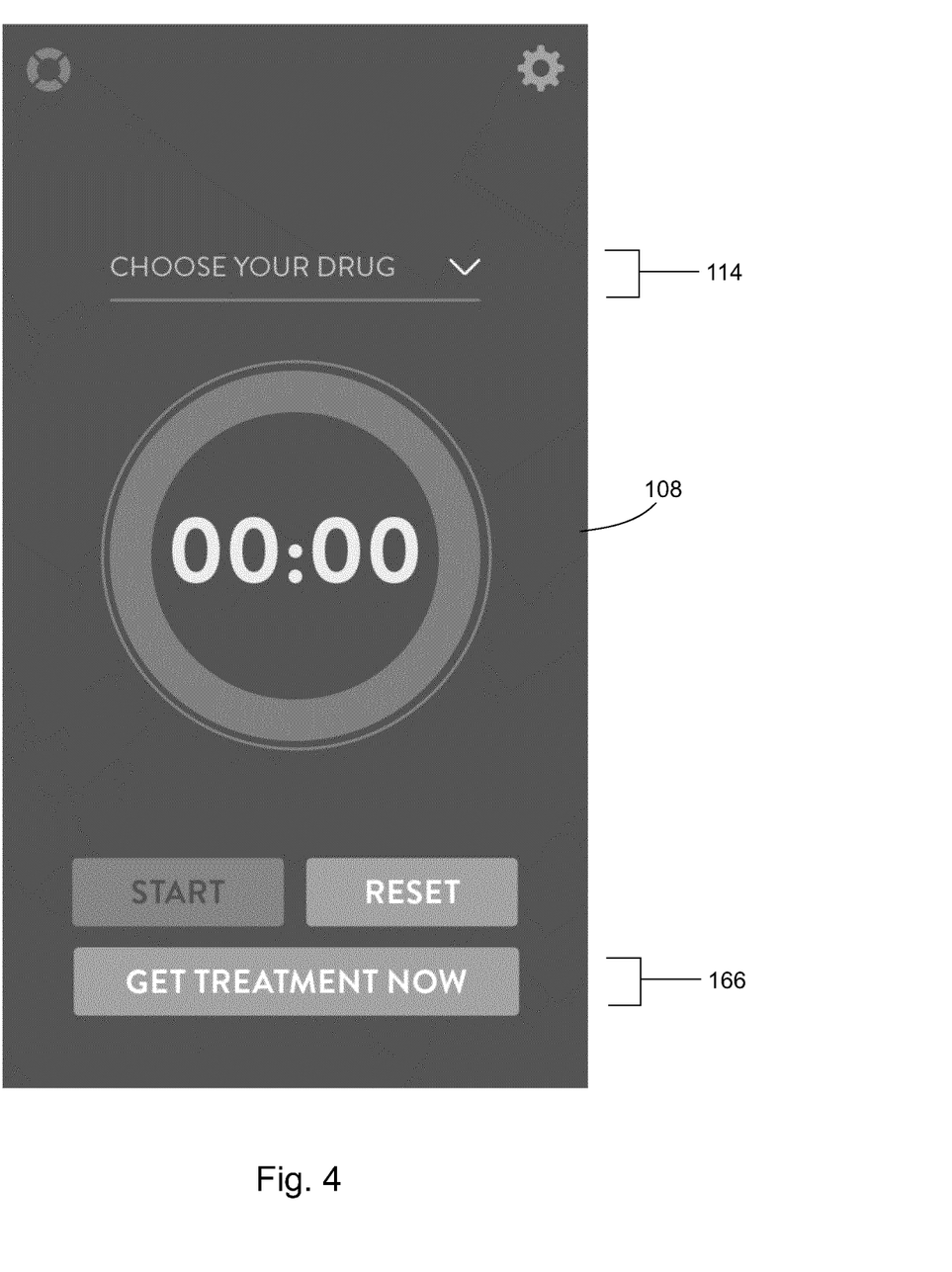
FIG. 4 is a screenshot depicting the user interface prompting the user to input the drug.
Figure 6:
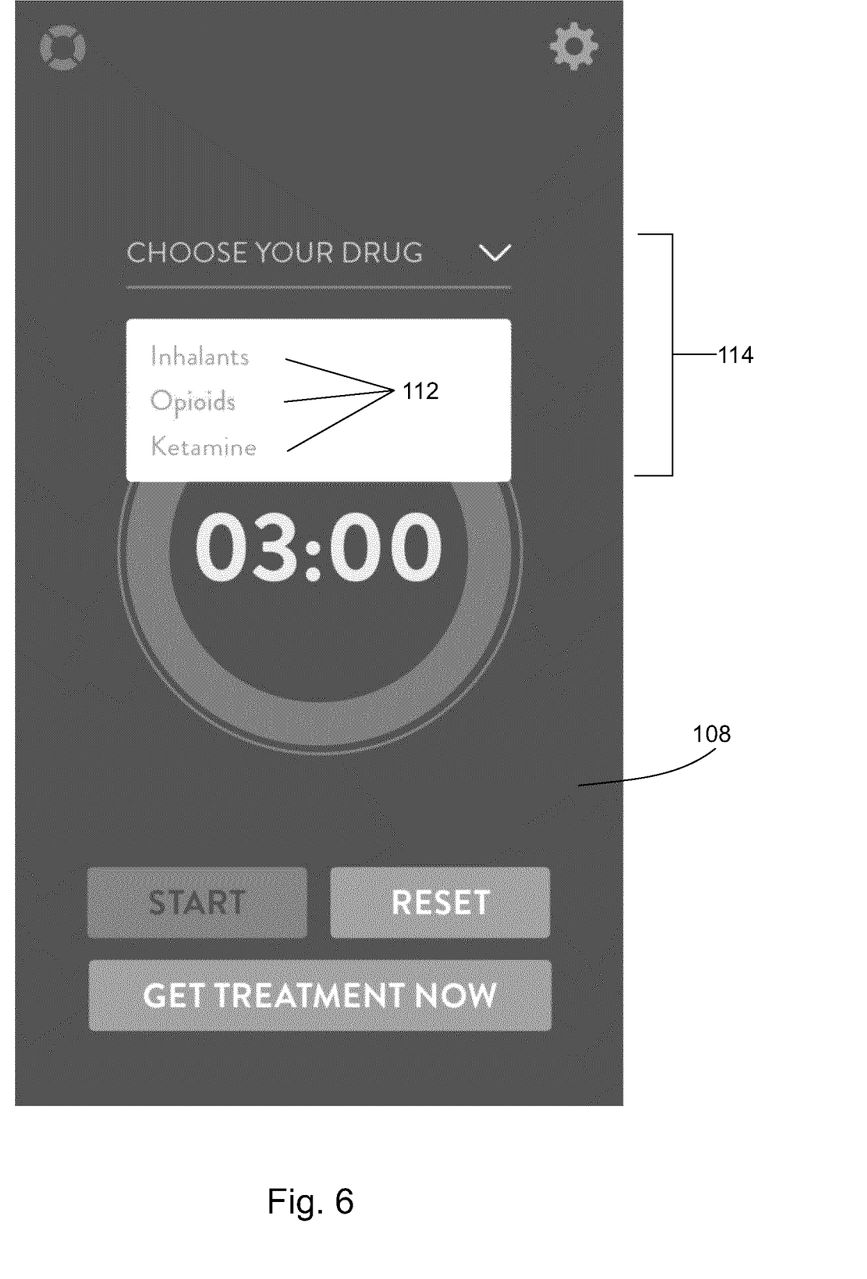
FIG. 6 is a screenshot depicting the user interface showing a menu for the user to select the drug.

Referring to FIG. 4, the user interface 108 will preferably prompt the user 104 to identify a drug 112. The drug 112 may be chosen from a drop-down menu 114 on the user interface 108 (as shown in FIG. 6), or it may be chosen in some other manner (e.g. through radio buttons, a text box, etc.).

Figure 5:
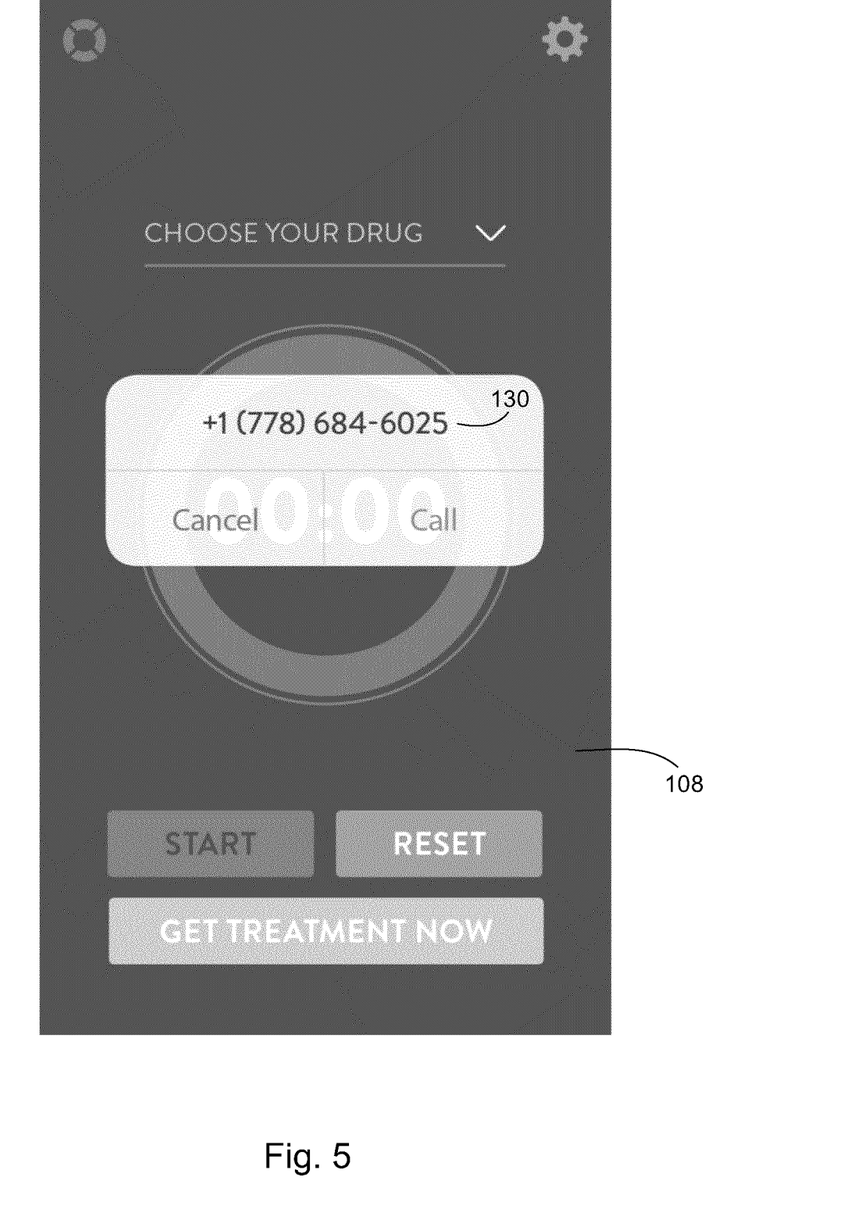
FIG. 5 is a screenshot depicting the user interface displaying information on treatment options.

Referring still to FIG. 4, the user interface 108 may also include the option for the user 104 to obtain information about medical treatment. For example, the user interface 108 may display a button (such as the medical treatment link 166) that will cause the user interface 108 to present information on treatment options (e.g. the button labelled "Get Treatment Now", as shown in FIG. 4 or some other appropriate button or text). If the user 104 selects this option, the user interface 108 preferably displays treatment information 130. This may include a phone number that the user 104 can call to obtain treatment, as shown in FIG. 5.

Figure 7:
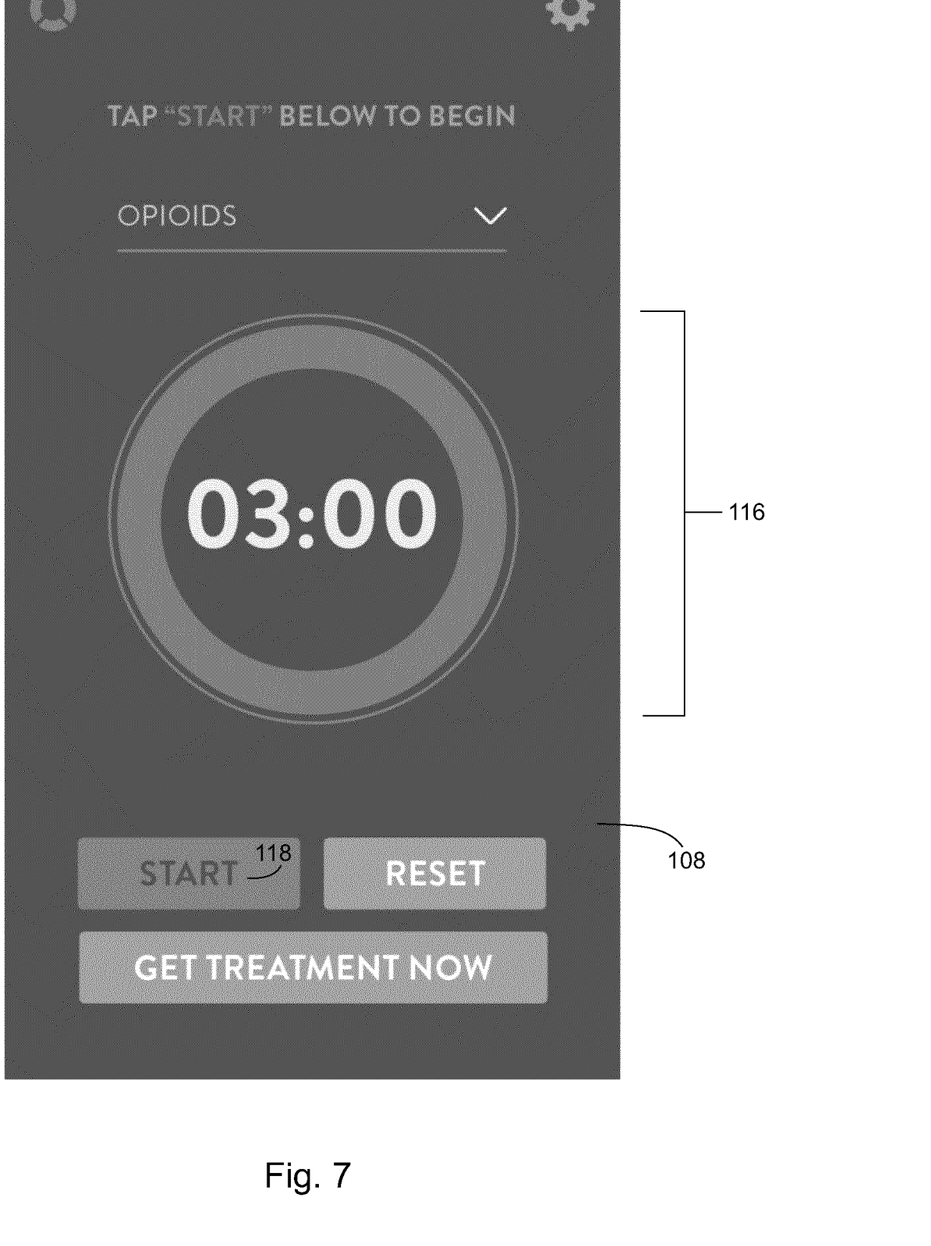
FIG. 7 is a screenshot depicting the user interface ready for the user to begin the start input.

Referring to FIG. 7, the user interface 108 preferably allows the user 104 to start a timer 116. This may be done through a start input 118 on the user interface 108. The start input 118 may be a button (e.g. the button labelled "Start" in FIG. 7), or it may be some other suitable input mechanism. The user 104 preferably starts the timer 116 before the drug 112 has been taken. Once the timer 116 has been started, the timer 116 will start counting down from a predetermined amount of time (e.g. 3 minutes, as shown in FIG. 7). Preferably, the user interface 108 displays the amount of time remaining for the timer 116. In addition, once the timer 116 has been started, the mobile application 100 preferably records the time of day of when the timer 116 was started.

In another embodiment, the user 104 may set the predetermined amount of time that the timer 116 will run for. For example, the user 104 may set the timer 116 to count down from 5 minutes, instead of 3 minutes.

Figure 8:
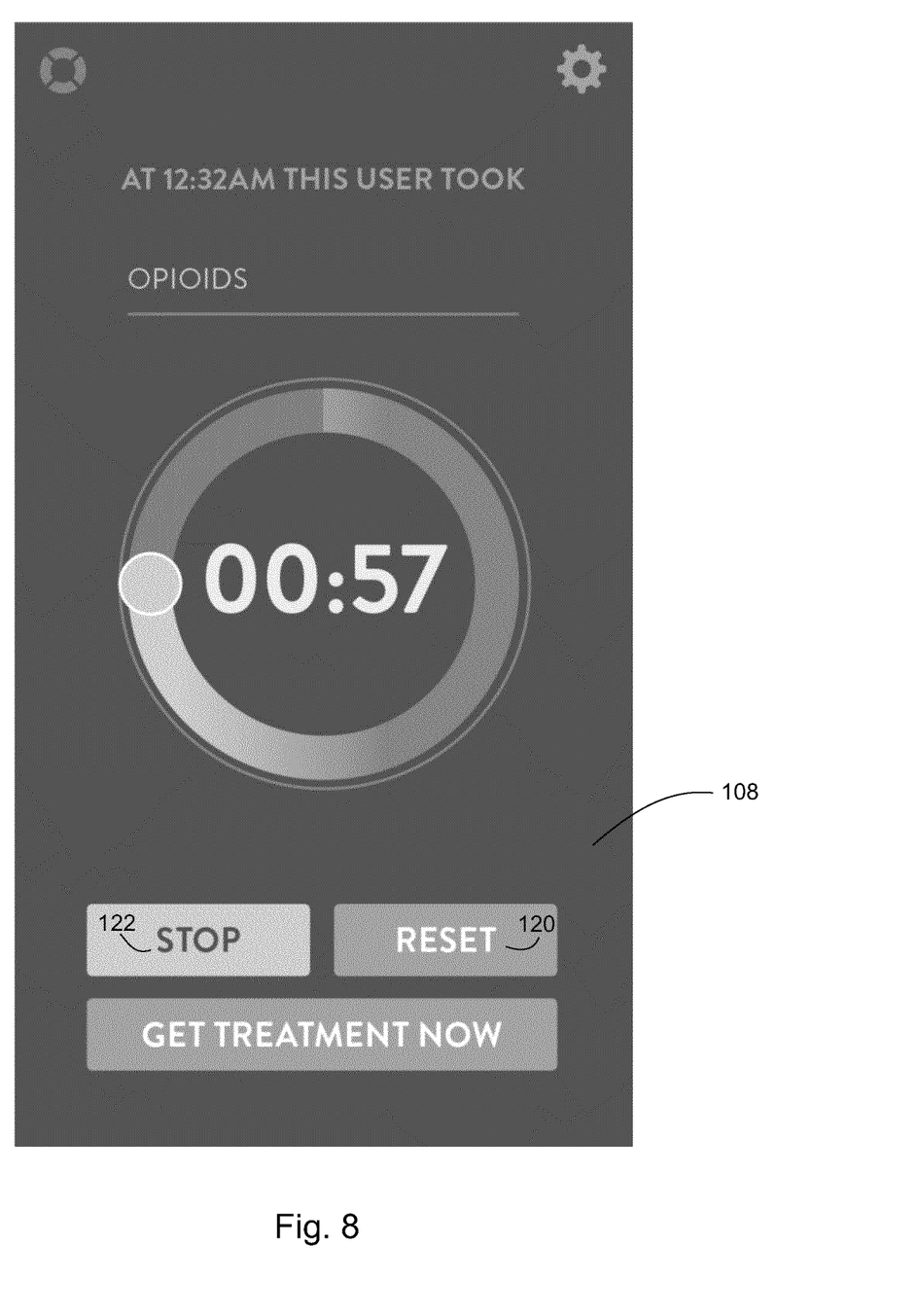
FIG. 8 is a screenshot depicting the user interface as the timer counts down.

Referring to FIG. 8, the user interface 108 may display the timer 116 as it continually counts down from the predetermined amount of time. At any time, the user 104 may use the reset input 120 to reset the timer 116 or a stop input 122 to stop the timer 116.

The user interface 108 preferably also allows the user 104 to reset the timer 116. This may be done through the reset input 120 on the user interface 108. For example, the reset input 120 may take the form of a button (e.g. the button labelled "Reset" in FIG. 8). This will reset the timer 116 to the predetermined amount of time.

The user interface 108 also allows the user 104 to stop the timer 116. This may be done through the stop input 122 on the user interface 108. For example, the stop input 122 may take the form of a button (e.g. the button labelled "Stop" in FIG. 8).

Figure 9:
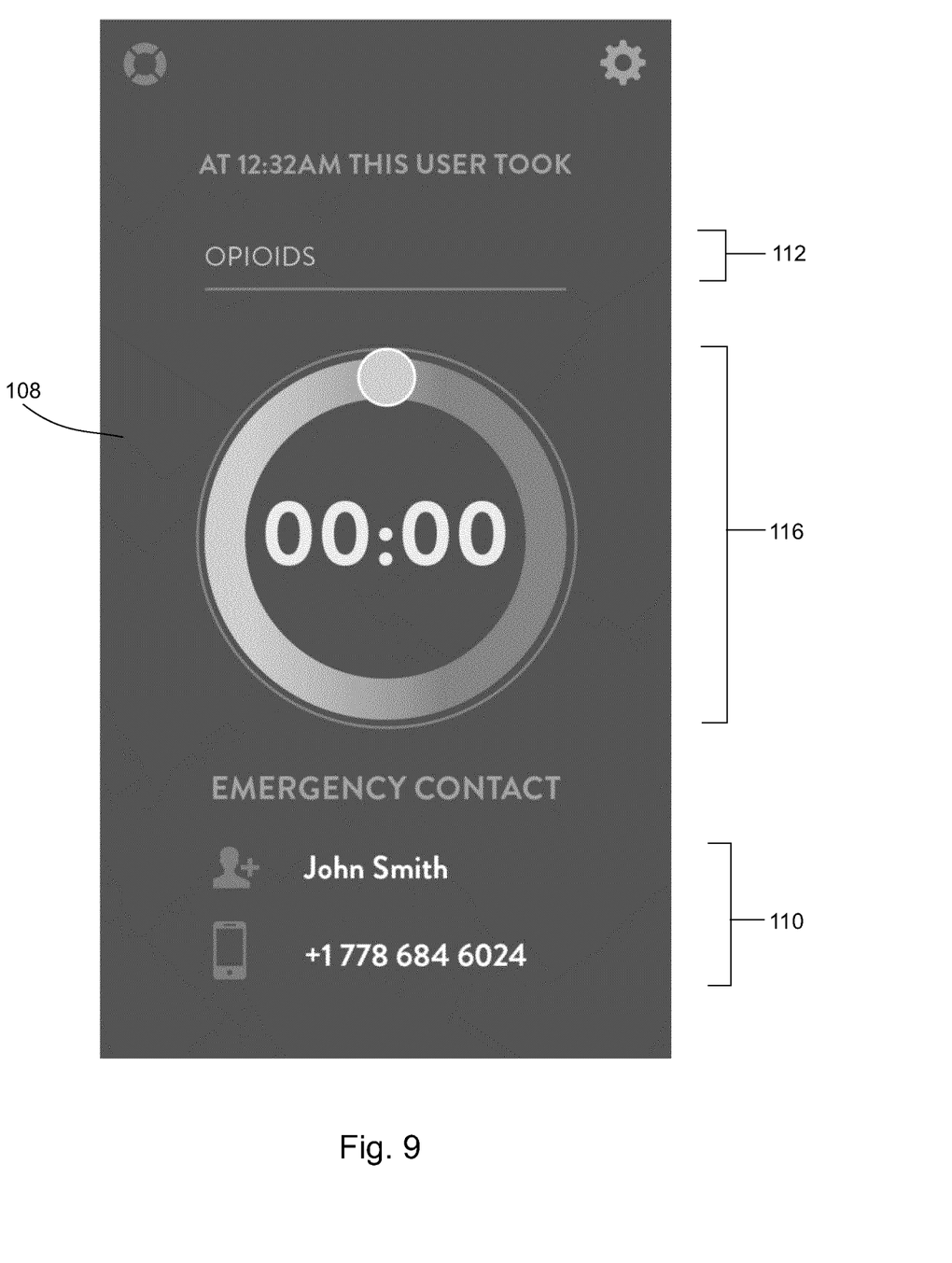
FIG. 9 is a screenshot depicting the user interface after the timer has finished counting down.

Referring to FIG. 9, if the timer 116 reaches zero time without the user 104 having activated the stop input 122, the user interface 108 preferably provides an alert to the user 104. The alert may take the form of one or more of the following: audio alert, visual alert, haptic alert, or vibration alert. For example, in one embodiment, the user interface 108 may display an appropriate symbol (e.g. a stop sign) to alert the user 104 of the expiry of the timer 116. The user 104 can then press on the symbol to reset the timer 116. In another embodiment, if the mobile device 102 comprises a light 125 (e.g. as part of a camera 124), the light 125 may be activated to provide further warning to the user 104 of the expiry of the timer 116.

If the mobile device 102 comprises camera 124 (e.g. a forward-facing camera), the mobile application 100 may cause the camera 124 to take a photograph or to start recording a video. If the mobile device 102 comprises a microphone 132, the mobile application 100 may cause the microphone 132 to start recording.

If the timer 116 reaches zero time without the user 104 having activated the stop input 122 or otherwise reset the timer 116, the mobile application 100 transmits a message 134 to remote server 150. The message 134 may be in the form of a text message. The message 134 preferably comprises some or all of the following information: the name of the user 104, the phone number of the mobile device 102, the location of the user 104 (as input by the user 104 or determined using the location detection sensors 126), the time at which the drug 112 was taken, and the name of the drug 112.

The remote server 150, upon receipt of the message 134, determines the appropriate emergency personnel 128 (e.g. the local 9-1-1 dispatcher for the user 104). This determination may be based, at least in part, on the location of the user 104. Once the appropriate emergency personnel 128 has been determined, the remote server 150 may convert the information in the message 134 into an audio message 136 that is suitable for transmission to the emergency personnel 128. This may be done using a text-to-voice converter 138. The remote server 150 then contacts the emergency personnel 128 (e.g. by telephone) and transmits the audio message 136 to the emergency personnel 128 for the appropriate emergency response. The audio message 136 may be continually repeated to ensure that the information therein is able to be properly recorded or noted by the emergency personnel 128.

The step of converting the message 134 to the audio message 136 may be necessary because the emergency personnel 128 may be unable to receive calls other than voice calls. However, if the emergency personnel 128 is equipped to handle other type of calls (e.g. text messages, data calls, etc.), then the step of converting the message 134 to the audio message 136 may be unnecessary, and the remote server 150 may transmit the message 134 directly to the emergency personnel 128 without any conversion.

In another embodiment, the remote server 150 is also to determine the nearest locations of naloxone kits (used for counteracting certain opioid overdoses). This information may be provided to the emergency personnel 128. Alternatively, this information may be shared with other people who have previously registered with the mobile application 100 and are nearby to the user 104 at that time.

The remote server 150 may also be able to determine the nearest locations of safe injection sites and display them (through the user interface 108 of the mobile application 100) to the user 104.

In one embodiment, the audio message 136 may comprise the phone number of the mobile device 102. If so, and if the emergency personnel 128 initiate a call to the mobile device 102, the mobile application 100 may automatically answer the call and relays any audio noise detected by the microphone 132 to the emergency personnel 128. In addition, any photographs or videos captured by the camera 124 may be made available to the emergency personnel 128 (through transmission or by other means).

If the timer 116 reaches zero time without the user 104 having activated the stop input 122, this is a possible indication that the user 104 has suffered a dangerous interaction with the drug 112 (e.g. an overdose). As the mobile application 100 is able to cause information to be transmitted to emergency personnel 128 without requiring any further input from the user 104, this ensures that emergency personnel 128 are notified even if the user 104 is physically unable to do so.

In another embodiment, in the event that the timer 116 reaches zero time without the user 104 having activated the stop input 122, the mobile application 100 contacts the emergency contact set out in the emergency contact information 110. For example, if the emergency contact information 110 comprises a phone number, the mobile application 100 may call the phone number and, using text-to-voice facilities, provide information to the emergency contact, such as the time at which the drug 112 was taken, the drug 112, and the location of the mobile device 102 (if applicable).

In a further embodiment, the mobile application 100 may provide a reminder to the user 104 after a set amount of time (e.g. 24 or 48 hours) after the drug 112 has been taken to prompt the user 104 to seek treatment or assistance. The mobile application 100 may also store a log of a history of the drug use by the user 104 and a history of locations of the user 104 when using the mobile application 100.

Figure 10:
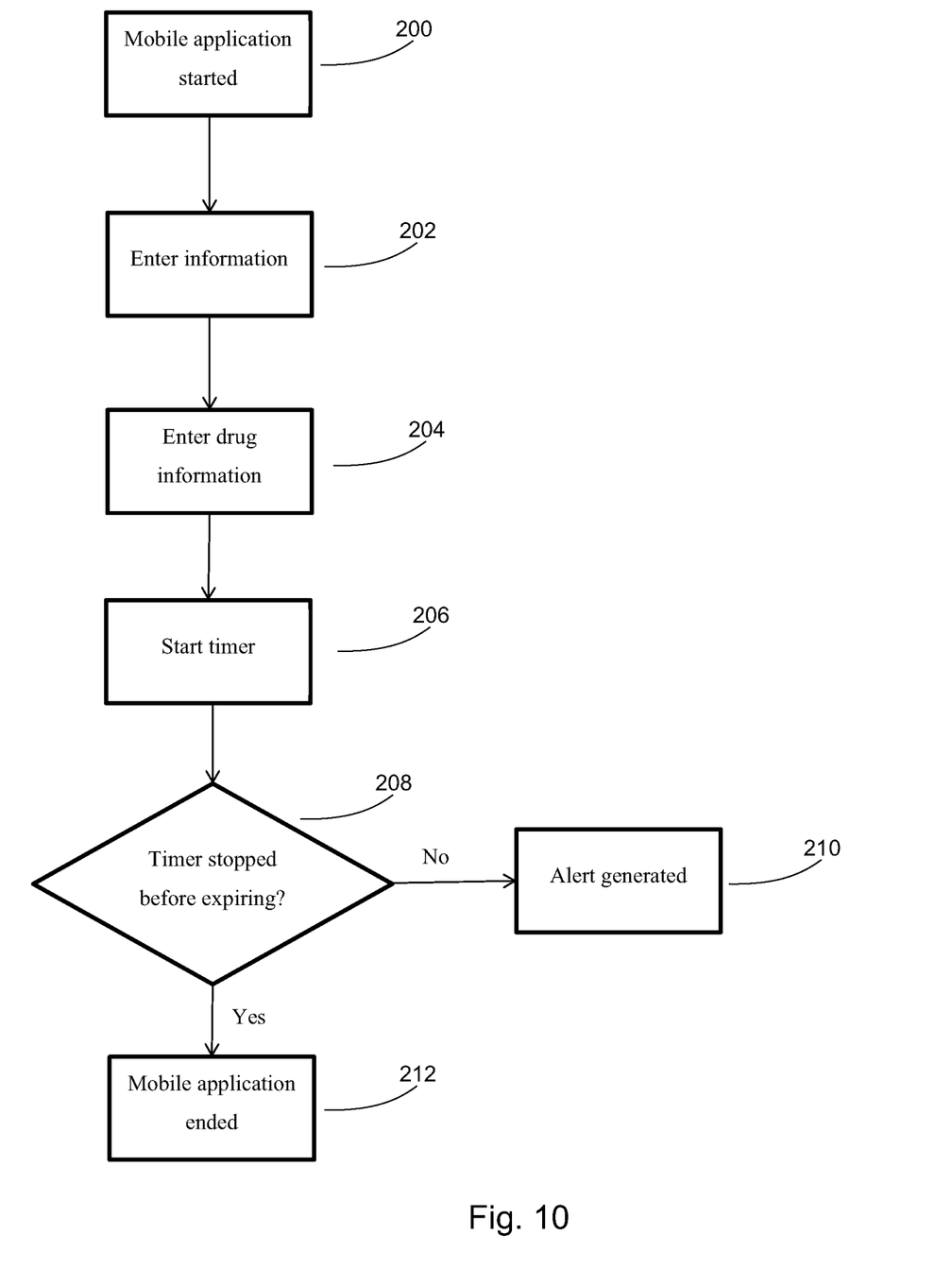
FIG. 10 depicts a flowchart showing the operation of the mobile application in accordance with the invention.

Referring to FIG. 10, a flowchart depicting the operation of the mobile application 100 is shown. At step 200, the mobile application 100 is executed by the user 104. At step 202, the user 104 is prompted by the mobile application 100 to input identifying information 105. At step 204, the user 104 is prompted by the mobile application 100 to input the name of the drug 112. At step 206, the user 104 is prompted by the mobile application 100 to start the timer 116 to run for a determined amount of time. At step 208, if the timer 116 reaches zero without the user 104 having stopped the timer 116 through the mobile application 100, an alert is generated. This alert may be communicated to the appropriate emergency personnel 128 for response. If the user 104 stops the timer 116 through the mobile application 100, the mobile application 100 ends.

It will be appreciated by those skilled in the art that the preferred embodiments have been described in some detail but that certain modifications may be practiced without departing from the principles of the invention.

The invention claimed is:

1. A method for alerting emergency personnel in the event of medical distress by a user, the method comprising:
   providing a mobile application for use on a mobile device, the mobile application configured to provide a user interface;
   initializing, by the user, of the mobile application on the mobile device;
   recording, by the mobile application, of a location of the user and a drug taken by the user;
   initiating, by the user, a timer on the user interface with a predetermined amount of time;
   upon the timer reaching the predetermined amount of time without the user interface receiving any further input from the user or from otherwise external to the mobile device, transmitting, by the mobile application, a first message to a remote server, the first message comprising the location of the user and the drug taken;
   converting, by the remote server, the first message into an audio message using a text-to-voice converter;
   contacting, by the remote server, a 9-1-1 dispatcher; and
   transmitting the audio message to the 9-1-1 dispatcher, wherein transmitting the audio message to the 9-1-1 dispatcher comprises continually repeating the audio message.

2. The method of claim 1, wherein the recording, by the mobile application, of the location of the user and the drug taken by the user further comprises recording of a name of the user and a current time.

3. The method of claim 1, wherein the location of the user may be determined by a location detection sensor located on the mobile device.

4. The method of claim 3, wherein the location detection sensor is a Global Positioning System sensor.

5. The method of claim 1, further comprising the step of contacting, by the 9-1-1 dispatcher, the user by telephone prior to dispatching emergency personnel to the location of the user.

\* \* \* \* \*